United States Patent [19]

Diana et al.

[11] 4,125,714

[45] Nov. 14, 1978

[54] ARYL SUBSTITUTED CYCLOALKANONES

[75] Inventors: Guy D. Diana, Stephentown; William B. Hinshaw, Jr., Sand Lake, both of N.Y.

[73] Assignee: Sterling Drug Inc., New York, N.Y.

[21] Appl. No.: 501,770

[22] Filed: Aug. 29, 1974

Related U.S. Application Data

[62] Division of Ser. No. 324,540, Jan. 17, 1973, Pat. No. 3,878,200.

[51] Int. Cl.$^2$ ..................... C07C 49/76; C07D 317/54
[52] U.S. Cl. ................................ 542/429; 260/590 C
[58] Field of Search .................. 260/340.5, 590 C; 542/429

[56] References Cited

U.S. PATENT DOCUMENTS 3,574,715  4/1971  Marbet ............................. 260/590 R

*Primary Examiner*—James O. Thomas, Jr.
*Assistant Examiner*—Michael Shippon
*Attorney, Agent, or Firm*—Thomas L. Johnson; B. Woodrow Wyatt

[57] ABSTRACT

Aryl substituted tertiary carbinols, useful as anti-viral agents and insecticides, are prepared by reacting the Grignard reagent derived from an arylalkyl or arylalkenyl iodide with a dialkyl ketone or an alkyl alkenyl ketone; or by reacting an arylalkyl or arylalkenyl ketone with an alkyl- or alkenylmagnesium halide. Corresponding cyclic tertiary carbinols are also prepared via intermediate cyclic ketones.

4 Claims, No Drawings

ARYL SUBSTITUTED CYCLOALKANONES

This application is a division of copending application Ser. No. 324,540, filed Jan. 17, 1973, now U.S. Pat. No. 3,878,200.

This invention relates to aryl substituted tertiary carbinols, to the preparation thereof and to certain novel intermediates.

The compounds of the invention are of the structural formula

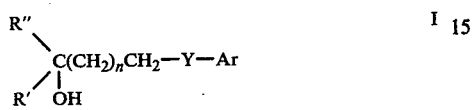

wherein Y is selected from the group consisting of:

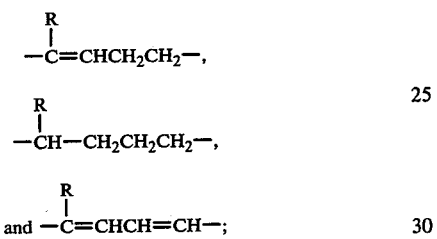

R' is lower-alkyl or lower-alkenyl of 1 to 4 carbon atoms;
R" is lower-alkyl of 1 to 4 carbon atoms;
$n$ is 1 or 2;
R' and R" can be joined to form a cyclopentane or cyclohexane ring;
R is hydrogen or lower-alkyl of 1 to 4 carbon atoms; and
Ar is phenyl or phenyl substituted by 3,4-methylenedioxy or one or two monovalent substituents selected from the group consisting of lower-alkyl of 1 to 4 carbon atoms, lower-alkoxy of 1 to 4 carbon atoms, halogen, trifluoromethyl and trifluoromethoxy.

The carbon chains of R, R', R" and Ar substituents can be straight or branched, although primary or secondary alkyl moieties are preferred.

When two monovalent substituents are present on the phenyl ring of Ar, they can be the same or different.

Intermediates for the compounds of the invention are prepared as described in the following reaction sequences.

Reaction Sequence A

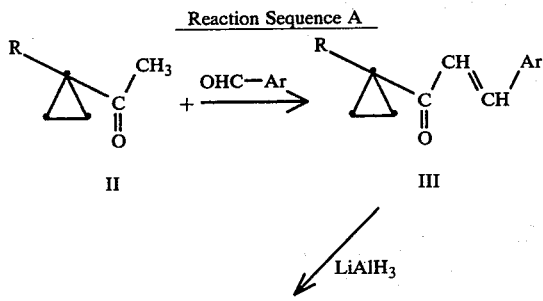

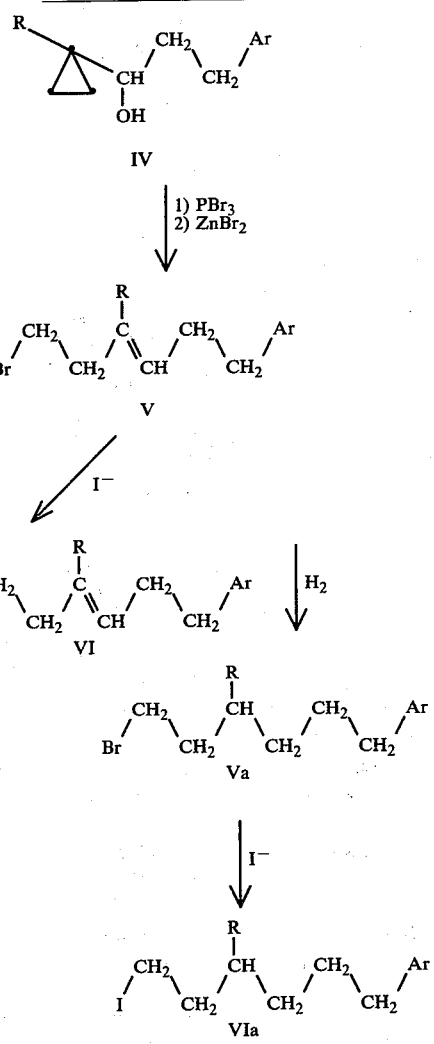

In the foregoing Reaction Sequence, A, a 1-R-1-acetylcyclopropane of formula II, where R has the meaning given hereinabove, is treated with an aldehyde ArCHO in the presence of a base to give the arylvinyl 1-R-cyclopropyl ketone of formula III. The latter, when treated with lithium aluminum hydride is reduced at both the carbonyl group and the olefinic linkage to give an arylethyl 1-R-cyclopropyl carbinol of formula IV. This carbinol is then treated with phosphorus tribromide in the presence of a metal bromide such as lithium bromide to replace the hydroxy group by bromine, which product is then treated with zinc bromide to effect ring opening to form an arylalkenyl bromide of formula V. The latter with a metallic iodide is converted to the corresponding iodide of formula VI. If a compound with a saturated alkylene chain is desired the unsaturated bromide of formula V is hydrogenated in the presence of palladium or platinum oxide catalyst or produce a saturated bromide of formula Va, which is in turn converted to the corresponding iodide VIa.

Reaction Sequence B

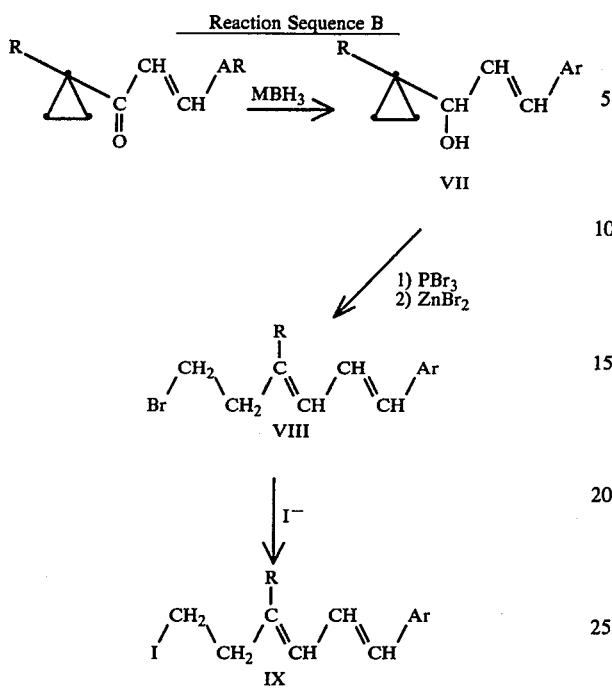

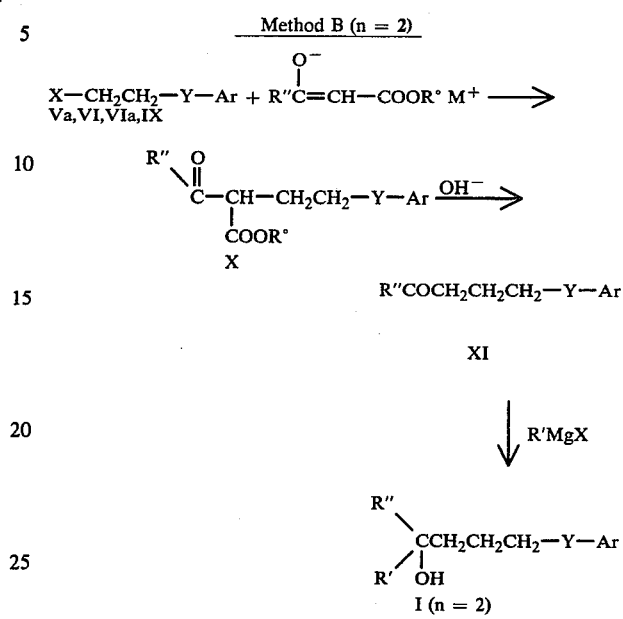

In Reaction Sequence B the arylvinyl 1-R-cyclopropyl ketone of formula III is treated with an alkali metal borohydride, preferably sodium borohydride, to reduce the carbonyl group but not the olefinic linkage and provide an arylvinyl 1-R-cyclopropyl carbinol of formula VII. By procedures analogous to those shown in Reaction Sequence A, the carbinol of formula VII is treated with phosphorus tribromide in the presence of a metal bromide and then with zinc bromide to give a diunsaturated aralkyl bromide of formula VIII. The latter is then converted to the corresponding iodide (IX).

The compounds of formula I can be prepared from the intermediates described above according to the following methods.

Method A (n = 1)

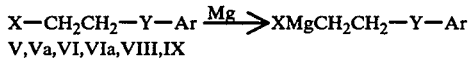

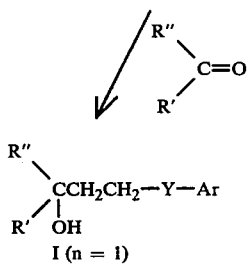

An arylalkyl halide or arylalkenyl halide of formula V, Va, VI, VIa, VIII or IX (X is Br or I) is converted to the corresponding Grignard reagent with magnesium metal by conventional means. The iodides, VI, VIa and IX are preferred because of their greater reactivity compared to the corresponding bromides. The Grignard reagent is then treated with a ketone of formula R'COR'', wherein R' and R'' have the meanings given hereinabove, to form a carbinol of formula I where $n$ is 1.

An iodide of formula VI, VIa or IX or a saturated bromide of formula Va is treated with the alkali metal (M) salt of a keto ester, R'' COCH$_2$COOR°, where R'' is lower-alkyl of 1 to 4 carbon atoms and R° is lower-alkyl of 1 to 6 carbon atoms. The alkali metal salt is preferably the lithium salt. The reaction takes place in an inert solvent under anhydrous conditions and produces a substituted keto ester of formula X. If the starting material is an iodide of formula VI, VIa or IX, the reaction takes place at temperatures of 20°–60° C., whereas if the starting material is a bromide of formula Va a higher temperature, about 100°–150° C. is required. The keto ester X is then hydrolyzed and decarboxylated by heating it in aqueous alkaline medium, preferably containing a lower-alkanol to provide a solvent for the keto ester. The resulting ketone of formula XI is then treated with a Grignard reagent R'MgX, wherein R' is lower-alkyl or lower-alkenyl of 1 to 4 carbon atoms and X is halogen, preferably bromine or iodine, to afford a compound of formula I where $n$ is 2.

The intermediate ketones of formula XI are novel and constitute a further aspect of the present invention.

The compounds of formula I where $n = 2$ and wherein R' and R'' are joined to form a cyclopentane or cyclohexane ring are readily prepared according to Method B, employing an alkali metal salt of a 2-carbo-lower-alkoxycycloalkanone of the formula

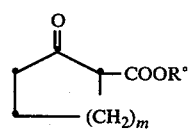

wherein $m$ is 1 or 2. Alkylation of the latter with a halide of formula Va, VI, VIa or IX affords a keto-ester of formula

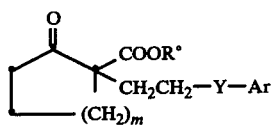

Hydrolysis and decarboxylation of the foregoing keto ester gives a cyclic ketone of the formula

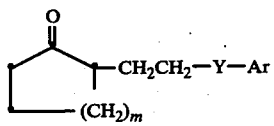 XIV which can be caused to react with a Grignard reagent, R'MgX, to produce a compound of formula I:

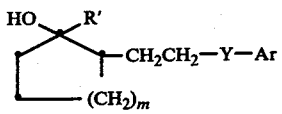 XV

The intermediate ketones of formula XIV are novel and constitute a further aspect of the present invention.

In a modification of the foregoing process the cyclic ketone of formula XIV can be prepared by heating a halide of formula Va, VI, VIa or IX with a cycloalkene enamine of the formula

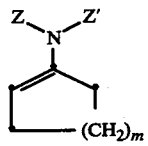

wherein Z and Z' are lower-alkyl groups optionally joined to form a heterocyclic ring. The pyrrolidine enamines are preferred reactants.

Biological evaluation of the compounds of the invention has shown that they possess antiviral activity. They have been found to be effective in vitro against one or more of a variety of viruses, including rhino-2, equine rhino, para-influenza and respiratory syncitial virus at minimal growth inhibitory concentrations (mic) ranging from about 0.3 to about 50 micrograms per milliliter. The mic values were determined by standard serial dilution procedures.

The compounds of the invention have also been found to possess pesticidal activity against arthropod species, as indicated by tests under simulated field conditions in a greenhouse against one or more of the following pest species: yellow mealworm pupae, dock beetle larvae, cabbage looper larvae, yellow fever mosquito larvae and rhodnius prolixus nymph.

The structures of the compounds of the invention were established by the modes of synthesis, by elementary analysis, and by infrared and nuclear magnetic resonance spectral determinations.

A further aspect of the invention relates to compositions for combatting arthropods by hindering the maturation thereof which comprise an effective amount of at least one compound of formula I in admixture with a suitable carrier or diluent, and to the method of combatting arthropods at any stage of their development by contacting them with said compositions.

The compositions of the invention are effective against insects at any stage of their development short of the final adult form, i.e. at the egg, larval or pupal stages. The compounds can be formulated in conventional manner as solutions, emulsions, suspensions, dusts and aerosol sprays. The pesticide compositions of the invention can contain adjuvants found normally in such preparations, including water and/or organic solvents such as acetone, dimethylformamide, sesame oil, petroleum oils, and the like. Emulsifying and surface active agents may also be added. Dust formulations can contain talc, diatomaceous earth, kaolin, bentonite, calcium carbonate, wood, flour, cork, carbon, and the like. The aerosol sprays contain propellants such as dichlorodifluoromethane. The compounds of this invention can be employed as the sole pesticide component or they can be used in admixture with other compounds having similar utility. While the concentration of active ingredient can vary within rather wide limits, ordinarily the pesticide will comprise not more than about 10%, and preferably about 1% by weight of the composition.

A still further aspect of the invention relates to compositions for combatting viruses which comprise an antivirally effective amount of at least one compound of formula I in admixture with a suitable carrier or diluent, and to the method of combatting viruses by contacting the locus of said viruses with said compositions.

The antiviral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams.

The following examples will further illustrate the invention.

PREPARATION OF INTERMEDIATES

A. 2-Arylvinyl cyclopropyl ketones (III)

A1. 2-(3,4-Methylenedioxyphenyl)vinyl 1-ethylcyclopropyl ketone [III; Ar is 3,4-methylenedioxyphenyl, R is $C_2H_5$].

A mixture of 33.6 g. (0.3 mole) of 1-ethylcyclopropyl methyl ketone and 45 g. (0.3 mole) of piperonal in 21 ml. of ethanol was stirred at room temperature, and 21 ml. of 20% aqueous sodium hydroxide was added dropwise over a period of 30–45 minutes. The mixture was warmed at 40°–60° C. for 3 hours with stirring. The solution was then cooled to 0°–10° C., 0.2 ml. of glacial acetic acid added, and the mixture was extracted with ether. The ether extracts were concentrated, and the residue dissolved in 200 ml. of 95% ethanol, which solution when cooled caused separation of a solid product. The latter was recrystallized from 150 ml. of methanol to give 39 g. of 2-(3,4-methylenedioxyphenyl)vinyl 1-ethylcyclopropyl ketone, m.p. 62°–64° C.

A2. 2-(3,4-Methylenedioxyphenyl)vinyl cyclopropyl ketone [III; Ar is 3,4-methylenedioxyphenyl, R is H] was prepared from 8.4 g. of cyclopropyl methyl ketone and 15 g. of piperonal according to the procedure described above in Preparation A1, affording 21.5 g., m.p. 85°–87° C. when recrystallized from ethanol.

A3. 2-(3,4-Methylenedioxyphenyl)vinyl 1-methylcyclopropyl ketone [III; Ar is 3,4-methylenedioxyphenyl, R is $CH_3$] was prepared from 25.6 g. of 1-methylcyclopropyl methyl ketone and 39.3 g. of piperonal according to the procedure described above in Preparation A1, affording 29.5 g. of crystalline product.

A4. 2-(3,4-Dimethoxyphenyl)vinyl 1-ethylcyclopropyl ketone [III; Ar is 3,4-$(CH_3O)_2C_6H_3$, R is $C_2H_5$] was prepared from 22.4 g. of 1-ethylcyclopropyl methyl ketone and 33.2 g. of veratraldehyde according to the procedure described above in Preparation A1, affording 20.3 g., b.p. 156°–158° C. (0.02 mm.).

A5. 2-(4-Methoxyphenyl)vinyl cyclopropyl ketone [III; Ar is 4-$CH_3OC_6H_4$, R is H] was prepared from 84.1 g. of cyclopropyl methyl ketone and 136 g. of p-methoxybenzaldehyde according to the procedure described above in Preparation A1, affording 173.5 1 g., m.p. 70°–72° C. when recrystallized from ethanol.

A6. 2-Phenylvinyl cyclopropyl ketone [III; Ar is $C_6H_5$, R is H] was prepared from 13.5 g. of cyclopropyl methyl ketone and 17.1 g. of benzaldehyde according to the procedure described above in Preparation A1, affording 23.0 g., m.p. 58°–60° C. when recrystallized from absolute ethanol.

A7. 2-(4-Chlorophenyl)vinyl cyclopropyl ketone [III; Ar is 4-$ClC_6H_4$, R is H] was prepared from 25.2 g. of cyclopropyl methyl ketone and 42 g. of p-chlorobenzaldehyde according to the procedure described above in Preparation A1, affording 31 g., m.p. 63°–65° C. when recrystallized from ethanol.

A8. 2-(p-Tolyl)vinyl cyclopropyl ketone [III; Ar is 4-$CH_3C_6H_4$, R is H] was prepared from 84.1 g. of cyclopropyl methyl ketone in 120 g. of p-tolualdehyde according to the procedure described above in Preparation A1, affording 158.7 g., colorless plates, m.p. 78°–80° C. when recrystallized from ethanol.

By following the procedure of Preparation A1 above, 1-isopropylcyclopropyl methyl ketone or 1-butylcyclopropyl methyl ketone can be caused to react with piperonal to give 2-(3,4-methylenedioxyphenyl)vinyl 1-isopropylcyclopropyl ketone [III; Ar is 3,4-methylenedioxyphenyl, R is $(CH_3)_2CH$], or 2-(3,4-methylenedioxyphenyl)vinyl 1-butylcyclopropyl ketone [III; Ar is 3,4-methylenedioxyphenyl, R is $CH_3CH_2CH_2CH_2$], respectively.

By following the procedure of Preparation A1 above, cyclopropyl methyl ketone can be caused to react with 3,4-dichlorobenzaldehyde, 2,4-dichlorobenzaldehyde, 4-bromobenzaldehyde, 4-fluorobenzaldehyde, 4-trifluoromethoxybenzaldehyde or 4-trifluoromethylbenzaldehyde to give, respectively:

2-(3,4-dichlorophenyl)vinyl cyclopropyl ketone [III; Ar is 3,4-$Cl_2C_6H_3$, R is H], 2-(2,4-dichlorophenyl)vinyl cyclopropyl ketone [III; Ar is 2,4-$Cl_2C_6H_3$, R is H], 2-(4-bromophenyl)vinyl cyclopropyl ketone [III; Ar is 4-$BrC_6H_4$, R is H], 2-(4-fluorophenyl)vinyl cyclopropyl ketone [III; Ar is 4-$FC_6H_4$, R is H], 2-(4-trifluoromethoxyphenyl)vinyl cyclopropyl ketone [III; Ar is 4-$F_3COC_6H_4$, R is H], or 2-(4-trifluoromethylphenyl)vinyl cyclopropyl ketone [III; Ar is 4-$F_3CC_6H_4$, R is H].

B. 2-Arylethyl cyclopropyl carbinols (IV) and 2arylvinyl cyclopropyl carbinols (VII)

B1. 2-(3,4-Methylenedioxyphenyl)ethyl 1-ethylcyclopropyl carbinol [IV; Ar is 3,4-methylenedioxyphenyl, R is $C_2H_5$].

A suspension of 15 g. of lithium aluminum hydride in about 500 ml. of tetrahydrofuran was heated at reflux while a solution of 60 g. of 2-(3,4-methylenedioxyphenyl)vinyl 1-ethylcyclopropyl ketone (Preparation A1) in 150 ml. of tetrahydrofuran was added dropwise over a period of 2–3 hours. The reaction mixture was heated at reflux for 2 hours, cooled, and then water was added very cautiously. Excess anhydrous sodium sulfate was added, the mixture filtered, and the filter cake washed several times with chloroform. The combined filtrate and washings were evaporated to dryness to give 53 g. of an oil consisting of 2-(3,4-methylenedioxyphenyl)ethyl 1-ethylcyclopropyl carbinol.

B2. 2-(3,4-Methylenedioxyphenyl)ethyl cyclopropyl carbinol [IV; Ar is 3,4-methylenedioxyphenyl, R is H] was prepared from 18.4 g. of 2-(3,4-methylenedioxyphenyl)vinyl cyclopropyl ketone (Preparation A2) and 3.1 g. of lithium aluminum hydride according to the procedure described above in Preparation B1, affording 11.5 g., b.p. 116°–122° C. (0.005 mm.), m.p. 64°–65° C. when recrystallized from ether.

B3. 2-(3,4-Methylenedioxyphenyl)ethyl 1-methylcyclopropyl carbinol [IV; Ar is 3,4-methylenedioxyphenyl, R is $CH_3$] was prepared from 23.4 g. of 2-(3,4-methylenedioxyphenyl)vinyl 1-methylcyclopropyl ketone (Preparation A3) and 3.88 g. of lithium aluminum hydride according to the procedure described above in Preparation B1, affording 18.8 g., b.p. 120°–130° C. (0.003 mm.).

B4. 2-(3,4-Dimethoxyphenyl)ethyl 1-ethylcyclopropyl carbinol [IV; Ar is 3,4-$(CH_3O)_2C_6H_3$, R is $C_2H_5$] was prepared from 15 g. of 2-(3,4-dimethoxyphenyl)vinyl 1-ethylcyclopropyl ketone (Preparation A4) and 2.2 g. of lithium aluminum hydride according to the procedure described above in Preparation B1, affording 10 g., b.p. 148°–150° C. (0.01 mm.).

B5. 2-(4-Methoxyphenyl)ethyl cyclopropyl carbinol [IV; Ar is 4-$CH_3OC_6H_4$, R is H] was prepared from 50 g. of 2-(4-methoxyphenyl)vinyl cyclopropyl ketone (Preparation A5) and 9.7 g. of lithium aluminum hydride according to the procedure described above in Preparation B1, affording 42 g., b.p. 116°–117° C. (0.05 mm.).

B6. 2-Phenylethyl cyclopropyl carbinol [IV; Ar is $C_6H_5$, R is H] was prepared from 23 g. of 2-phenylvinyl cyclopropyl ketone (Preparation A6) and 5.22 g. of lithium aluminum hydride according to the procedure described above in Preparation B1, affording 18.5 g., b.p. 89°–90° C. (0.02 mm.).

B7. 2-(4-Chlorophenyl)ethyl cyclopropyl carbinol [IV; Ar is 4-$ClC_6H_4$, R is H] was prepared from 31 g. of 2-(4-chlorophenyl)vinyl cyclopropyl ketone (Preparation A7) and 5.87 g. of lithium aluminum hydride according to the procedure described above in Preparation B1, affording 23.8 g., b.p. 105°–106° C. (0.1 mm.).

B8. 2-(p-Tolyl)ethyl cyclopropyl carbinol [IV; Ar is 4-$CH_3C_6H_4$, R is H] was prepared from 158 g. of 2-(p-tolyl)vinyl cyclopropyl ketone (Preparation A8) and 33.2 g. of lithium aluminum hydride according to the procedure described above in Preparation B1, affording 137 g., b.p. 97°–98° C. (0.13 mm.).

B9. 2-(3,4-Methylenedioxyphenyl)vinyl 1-ethylcyclopropyl carbinol [VII; Ar is 3,4-methylenedioxyphenyl, R is $C_2H_5$].

To a cold solution of 5 g. of 2-(3,4-methylenedioxyphenyl)vinyl 1-ethylcyclopropyl ketone (Preparation A1) in 50 ml. of methanol was added in portions 1.56 g. of sodium borohydride. The mixture was stirred at room temperature for 2 hours, then diluted with water and extracted with ether. The ether extracts were dried and concentrated to give 3.6 g. of 2-(3,4-methylenedioxyphenyl)vinyl 1-ethylcyclopropyl carbinol as a colorless oil.

By replacing the 2-(3,4-methylenedioxyphenyl)vinyl 1-ethylcyclopropyl ketone in Preparation B1 above by a molar equivalent amount of 2-(3,4-methylenedioxyphenyl)vinyl 1-isopropylcyclopropyl ketone, 2-(3,4-methylenedioxyphenyl)vinyl 1-butylcyclopropyl ketone, 2-(3,4-dichlorophenyl)vinyl cyclopropyl ketone, 2-(2,4-dichlorophenyl)vinyl cyclopropyl ketone, 2-(4-bromophenyl)vinyl cyclopropyl ketone, 2-(4-fluorophenyl)vinyl cyclopropyl ketone, 2-(4-trifluoromethoxyphenyl)vinyl cyclopropyl ketone or 2-(4-trifluoromethylphenyl)vinyl cyclopropyl ketone there can be obtained, respectively:

2-(3,4-methylenedioxyphenyl)ethyl 1-isopropylcyclopropyl carbinol [IV; Ar is 3,4-methylenedioxyphenyl, R is $(CH_3)_2CH$], 2-(3,4-methylenedioxyphenyl)ethyl 1-butylcyclopropyl carbinol [IV; Ar is 3,4-methylenedioxyphenyl, R is $CH_3CH_2CH_2CH_2$], 2-(3,4-dichlorophenyl)ethyl cyclopropyl carbinol [IV; Ar is 3,4-$Cl_2C_6H_3$, R is H], 2-(2,4-dichlorophenyl)ethyl cyclopropyl carbinol [IV; Ar is 2,4-$Cl_2C_6H_3$, R is H], 2-(4-bromophenyl)ethyl cyclopropyl carbinol [IV; Ar is 4-$BrC_6H_4$, R is H], 2-(4-fluorophenyl)ethyl cyclopropyl carbinol [IV; Ar is 4-$FC_6H_4$, R is H], 2-(4-trifluoromethoxyphenyl)ethyl cyclopropyl carbinol [IV; Ar is 4-$F_3COC_6H_4$, R is H], or 2-(4-trifluoromethylphenyl)ethyl cyclopropyl carbinol [IV; Ar is 4-$F_3CC_6H_4$, R is H].

C. Arylalkenyl bromides (V, VIII) and arylalkyl bromides (Va)

C1. 3-Ethyl-6-(3,4-methylenedioxyphenyl)-3-hexenyl bromide [V; Ar is 3,4-methylenedioxyphenyl, R is $C_2H_5$].

To a solution of 26.4 g. (0.106 mole) of 2-(3,4-methylenedioxyphenyl)ethyl 1-ethylcyclopropyl carbinol in 250 ml. of ether, cooled to −30° C. under nitrogen, was added 18 ml. of collidine. Lithium bromide (26 g., 0.3 mole) was then added, the mixture cooled to −50° C. and 25 g. (0.09 mole) of phosphorus tribromide was added dropwise. The reaction mixture was stirred at −50° C. for 10 minutes, allowed to warm to 0° C. over a 3 hour period and stirred at 0° C. for 3 hours. Collidine (30 ml.) was added, followed by 10 ml. of water. The reaction mixture was partitioned between water and ether, the ether layer washed with water and sodium chloride solution, and dried over anhydrous magnesium sulfate. The ether solution was concentrated to give an oily product used directly in the following reaction.

The latter product was dissolved in about 200 ml. of anhydrous ether and added in a fine stream to a stirred mixture of 27 g. of zinc bromide in 200 ml. of ether held at −30° to −35° C. The mixture was stirred, then allowed to warm to 0° C. during 2 hours, held there for 30 minutes, and then allowed to warm to room temperature over a 3 hour period and stirred for 2 hours longer. The reaction mixture was partitioned between ether and aqueous sodium chloride. The ether layer was washed three times with 500 ml. of water, then with sodium chloride solution, dried over anhydrous magnesium sulfate and concentrated to remove the solvent. The residue was redissolved in ether, washed with dilute aqueous sodium bicarbonate and with sodium chloride solution, and evaporated to give 23 g. of 3-ethyl-6-(3,4-methylenedioxyphenyl)-3-hexenyl bromide as a straw-colored oil.

C2. 6-(3,4-Methylenedioxyphenyl)-3-hexenyl bromide [V; Ar is 3,4-methylenedioxyphenyl, R is H] was prepared from 11.5 g. of 2-(3,4-methylenedioxyphenyl)ethyl cyclopropyl carbinol (Preparation B2), 12 g. of phosphorus tribromide, 10 g. of lithium bromide and 12.7 g. of zinc bromide according to the procedure given above in Preparation C1, affording 12.5 g. of product as an oil.

C3. 3-Methyl-6-(3,4-methylenedioxyphenyl)-3-hexenyl bromide [V; Ar is 3,4-methylenedioxyphenyl, R is $CH_3$] was prepared from 17.6 g. of 2-(3,4-methylenedioxyphenyl)ethyl 1-methylcyclopropyl carbinol (Preparation B3), 20.3 g. of phosphorus tribromide, 18.5 g. of lithium bromide and 21 g. of zinc bromide according to the procedure given above the Preparation C1, affording 19 g. of product as an oil.

C4. 3-Ethyl-6-(3,4-dimethoxyphenyl)-3-hexenyl bromide [V; Ar is 3,4-$(CH_3O)_2C_6H_3$, R is $C_2H_5$] was prepared from 16 g. of 2-(3,4-dimethoxyphenyl)ethyl 1-ethylcyclopropyl carbinol (Preparation B4), 16.8 g. of phosphorus tribromide, 16.8 g. of lithium bromide and 17.6 g. of zinc bromide according to the procedure given above in Preparation C1. The product was used directly in the succeeding step (Preparation D4) without isolation.

C5. 6-(4-Methoxyphenyl)-3-hexenyl bromide [V; Ar is 4-$CH_3OC_6H_4$, R is H] was prepared from 38.2 g. of 2-(4-methoxyphenyl)ethyl cyclopropyl carbinol (Preparation B5), 42.5 g. of phosphorus tribromide, 35 g. of lithium bromide and 40 g. of zinc bromide according to the procedure given above in Preparation C1, affording 48 g. of product as an oil.

C6. 6-Phenyl-3-hexenyl bromide [V; Ar is $C_6H_5$, R is H] was prepared from 16.5 g. of 2-phenylethyl cyclopropyl carbinol (Preparation B6), 21.5 g. of phosphorus tribromide, 17.65 g. of lithium bromide and 20.7 g. of zinc bromide according to the procedure given above in Preparation C1, affording 21 g. of product as a pale yellow oil.

C7. 6-(4-Chlorophenyl)-3-hexenyl bromide [V; Ar is 4-$ClC_6H_4$, R is H] was prepared from 21 g. of 2-(4-chlorophenyl)ethyl cyclopropyl carbinol (Preparation B7), 23 g. of phosphorus tribromide, 18.85 g. of lithium bromide and 22.5 g. of zinc bromide according to the procedure given above in Preparation C1, affording 25.5 g. of product as an oil.

C8. 6-(p-Tolyl)-3-hexenyl bromide [V; Ar is 4-$CH_3C_6H_4$, R is H] can be prepared from 2-(p-tolyl)ethyl cyclopropyl carbinol (Preparation B8), phosphorus tribromide, lithium bromide and zinc bromide according to the procedure given above in Preparation C1.

C9. 3-Ethyl-6-(3,4-methylenedioxyphenyl)-3,5-hexadienyl bromide [VIII; Ar is 3,4-methylenedioxyphenyl, R is $C_2H_5$] was prepared from 3.6 g. of 2-(3,4-methylenedioxyphenyl)vinyl 1-ethylcyclopropyl carbinol (Preparation B9), 3.5 g. of phosphorus tribromide, 4.5 g. of lithium bromide and 3.5 g. of zinc bromide according to the procedure given above in Preparation C1, affording 2 g. of product as an oil.

C10. 6-(4-Methoxyphenyl)hexyl bromide [V$a$; Ar is 4-CH$_3$OC$_6$H$_4$, R is H].

A mixture of 18.6 g. of 6-(4-methoxyphenyl)-3-hexenyl bromide (Preparation C5) and 0.21 g. of platinum oxide catalyst in 200 ml. of isopropyl alcohol was hydrogenated until 1 mole equivalent of hydrogen had been absorbed. The product was isolated and distilled to give 12.8 g. of 6-(4-methoxyphenyl)hexyl bromide, b.p. 126°–128° C. (0.04 mm.).

C11. 6-Phenylhexyl bromide [V$a$; Ar is C$_6$H$_5$, R is H] was prepared by hydrogenation of 21 g. of 6-phenyl-3-hexenyl bromide (Preparation C6) according to the procedure described above in Preparation C10, affording 16 g., b.p. 86°–87° C. (0.02 mm.).

C12. 6-(4-Chlorophenyl)hexyl bromide [V$a$; Ar is 4-ClC$_6$H$_4$, R is H] was prepared by hydrogenation of 25.2 g. of 6-(4-chlorophenyl)-3-hexenyl bromide (Preparation C7) according to the procedure described above in Preparation C10, affording 17 g., b.p. 110°–111° C. (0.02 mm.).

C13. 6-(p-Tolyl)hexyl bromide [V$a$; Ar is 4-CH$_3$C$_6$H$_4$, R is H] can be prepared by hydrogenation of 6-(p-tolyl)-3-hexenyl bromide according to the procedure described above in Preparation C10.

By replacing the 2-(3,4-methylenedioxyphenyl)ethyl 1-ethylcyclopropyl carbinol in Preparation C1 by a molar equivalent amount of 2-(3,4-methylenedioxyphenyl)ethyl 1-isopropylcyclopropyl carbinol, 2-(3,4-methylenedioxyphenyl)ethyl 1-butylcyclopropyl carbinol, 2-(3,4-dichlorophenyl)ethyl cyclopropyl carbinol, 2-(2,4-dichlorophenyl)ethyl cyclopropyl carbinol, 2-(4-bromophenyl)ethyl cyclopropyl carbinol, 2-(4-fluorophenyl)ethyl cyclopropyl carbinol, 2-(4-trifluoromethoxyphenyl)ethyl cyclopropyl carbinol or 2-(4-trifluoromethylphenyl)ethyl cyclopropyl carbinol there can be obtained, respectively:

3-isopropyl-6-(3,4-methylenedioxyphenyl)-3hexenyl bromide [V; Ar is 3,4-methylenedioxyphenyl, R is (CH$_3$)$_2$CH], 3-butyl-6-(3,4-methylenedioxyphenyl)-3-hexenyl bromide [V; Ar is 3,4-methylenedioxyphenyl, R is CH$_3$CH$_2$CH$_2$CH$_2$], 6-(3,4-dichlorophenyl)-3-hexenyl bromide [V; Ar is 3,4-Cl$_2$C$_6$H$_3$, R is H], 6-(2,4-dichlorophenyl)-3-hexenyl bromide [V; Ar is 2,4-Cl$_2$C$_6$H$_3$, R is H], 6-(4-bromophenyl)-3-hexenyl bromide [V; Ar is 4-BrC$_6$H$_4$, R is H], 6-(4-fluorophenyl)-3-hexenyl bromide [V; Ar is 4-FC$_6$H$_4$, R is H], 6-(4-trifluoromethoxyphenyl)-3-hexenyl bromide [V; Ar is 4-F$_3$COC$_6$H$_4$, R is H], or 6-(4-trifluoromethylphenyl)-3-hexenyl bromide [V; Ar is 4-F$_3$CC$_6$H$_4$, R is H].

The latter products can be hydrogenated according to the procedure of Preparation C10 to give, respectively:

3-isopropyl-6-(3,4-methylenedioxyphenyl)hexyl bromide [V$a$; Ar is 3,4-methylenedioxyphenyl, R is (CH$_3$)$_2$CH], 3-butyl-6-(3,4-methylenedioxyphenyl)hexyl bromide [V$a$; Ar is 3,4-methylenedioxyphenyl, R is CH$_3$CH$_2$CH$_2$CH$_2$], 6-(3,4-dichlorophenyl)hexyl bromide [V$a$; Ar is 3,4-Cl$_2$C$_6$H$_3$, R is H], 6-(2,4-dichlorophenyl)hexyl bromide [V$a$; Ar is 2,4-Cl$_2$C$_6$H$_3$, R is H], 6-(4-bromophenyl)hexyl bromide [V$a$; Ar is 4-BrC$_6$H$_4$, R is H], 6-(4-fluorophenyl)hexyl bromide [V$a$; Ar is 4-FC$_6$H$_4$, R is H], 6-(4-trifluoromethoxyphenyl)hexyl bromide [V$a$; Ar is 4-F$_3$COC$_6$H$_4$, R is H], or 6-(4-trifluoromethylphenyl)hexyl bromide [V$a$; Ar is 4-F$_3$CC$_6$H$_4$, R is H].

D. Arylalkenyl iodides (VI, IX) and arylalkyl iodides (VI$a$)

D1. 3-Ethyl-6-(3,4-methylenedioxyphenyl)-3-hexenyl iodide [VI; Ar is 3,4-methylenedioxyphenyl, R is C$_2$H$_5$].

A mixture of 23 g. of 3-ethyl-6-(3,4-methylenedioxyphenyl)-3-hexenyl bromide (Preparation C1) and 30 g. of powdered potassium iodide in 250 ml. of dimethylformamide was stirred for about 16 hours. The reaction mixture was concentrated to remove the solvent and the residue partitioned between cyclohexane and water. The cyclohexane layer was separated, dried over anhydrous magnesium sulfate and evaporated to give 33.0 g. of 3-ethyl-6-(3,4-methylenedioxyphenyl)-3-hexenyl iodide as a light yellow oil.

D2. 6-(3,4-Methylenedioxyphenyl)-3-hexenyl iodide [VI; Ar is 3,4-methylenedioxyphenyl, R is H] was prepared from 12.9 g. of 6-(3,4-methylenedioxyphenyl)-3-hexenyl bromide (Preparation C2) and 7 g. of sodium iodide in 120 ml. of acetone, refluxed for three hours, affording 12.5 g. of product as an oil.

D3. 3-Methyl-6-(3,4-methylenedioxyphenyl)-3-hexenyl iodide [VI; Ar is 3,4-methylenedioxyphenyl, R is CH$_3$] was prepared from 19.0 g. of 3-methyl-6-(3,4-methylenedioxyphenyl)-3-hexenyl bromide (Preparation C3) and 10.5 g. of sodium iodide in 125 ml. of acetone, to give 21 g. of product as a yellow oil.

D4. 3-Ethyl-6-(3,4-dimethoxyphenyl)-3-hexenyl iodide [VI; Ar is 3,4-(CH$_3$O)$_2$C$_6$H$_3$, R is C$_2$H$_5$] was prepared from 13.8 g. of 3-ethyl-6-(3,4-dimethoxyphenyl)-3-hexenyl bromide (Preparation C4) and 9 g. of sodium iodide in 120 ml. of acetone, to give 15 g. of product as an oil.

D5. 6-(4-Methoxyphenyl)-3-hexenyl iodide [VI; Ar is 4-CH$_3$OC$_6$H$_4$, R is H] was prepared from 24 g. of 6-(4-methoxyphenyl)-3-hexenyl bromide (Preparation C5) and 14.75 g. of sodium iodide in 475 ml. of 2-butanone, to give 28.5 g. of product as an oil.

D6. 6-(4-Methoxyphenyl)hexyl iodide [VI$a$; Ar is 4-CH$_3$OC$_6$H$_4$, R is H] was prepared from 16.5 g. of 6-(4-methoxyphenyl)hexyl bromide (Preparation C10) and 9.93 g. of sodium iodide in 325 ml. of 2-butanone, to give 19.3 g. of product as a pale yellow oil.

D7. 6-Phenylhexyl iodide [VI$a$; Ar is C$_6$H$_5$, R is H] was prepared from 16 g. of 6-phenylhexyl bromide (Preparation C11) and 10.95 g. of sodium iodide in 325 ml. of 2-butanone, to give 19.1 g. of product as an oil.

D8. 6-(4-Chlorophenyl)hexyl iodide [VI$a$; Ar is 4-ClC$_6$H$_4$, R is H] was prepared from 17 g. of 6-(4-chlorophenyl)hexyl bromide (Preparation C12) and 10.2 g. of sodium iodide in 325 ml. of acetone, to give 21 g. of product as an oil.

D9. 6-(p-Tolyl)hexyl iodide [VI$a$; Ar is 4-CH$_3$C$_6$H$_4$, R is H] can be prepared from 6-(p-tolyl)hexyl bromide (Preparation C13) and sodium iodide in acetone according to the procedure of Preparation D2 above.

D10. 3-Ethyl-6-(3,4-methylenedioxyphenyl)-3,5-hexadienyl iodide [IX; Ar is 3,4-methylenedioxyphenyl, R is $C_2H_5$] was prepared from 10 g. of 3-ethyl-6-(3,4-methylenedioxyphenyl)-3,5-hexadienyl bromide (Preparation C9) and 6 g. of sodium iodide in 120 ml. of acetone, to give 10.5 g. of product as an oil.

By similar procedures 3-isopropyl-6-(3,4-methylenedioxyphenyl)hexyl bromide, 3-butyl-6-(3,4-methylenedioxyphenyl)hexyl bromide, 6-(3,4-dichlorophenyl)hexyl bromide, 6-(2,4-dichlorophenyl)hexyl bromide, 6-(4-bromophenyl)hexyl bromide, 6-(4-fluorophenyl)hexyl bromide, 6-(4-trifluoromethoxyphenyl)hexyl bromide, or 6-(4-trifluoromethylphenyl)hexyl bromide can be caused to react with sodium iodide or give, respectively:

3-isopropyl-6-(3,4-methylenedioxyphenyl)hexyl iodide [VIa; Ar is 3,4-methylenedioxyphenyl, R is $(CH_3)_2CH$], 3-butyl-6-(3,4-methylenedioxyphenyl)hexyl iodide [VIa; Ar is 3,4-methylenedioxyphenyl, R is $CH_3CH_2CH_2CH_2$], 6-(3,4-dichlorophenyl)hexyl iodide [VIa; Ar is 3,4-$Cl_2C_6H_3$, R is H], 6-(2,4-dichlorophenyl)hexyl iodide [VIa; Ar is 2,4-$Cl_2C_6H_3$, R is H], 6-(4-bromophenyl)hexyl iodide [VIa; Ar is 4-$BrC_6H_4$, R is H], 6-(4-fluorophenyl)hexyl iodide [VIa; Ar is 4-$FC_6H_4$, R is H], 6-(4-trifluoromethoxyphenyl)hexyl iodide [VIa; Ar is 4-$F_3COC_6H_4$, R is H], or 6-(4-trifluoromethylphenyl)hexyl iodide [VIa; Ar is 4-$F_3CC_6H_4$, R is H].

EXAMPLE 1

6-Ethyl-3-methyl-9-(3,4-methylenedioxyphenyl)-6-nonen-3-ol [I; Ar is 3,4-methylenedioxyphenyl, R' is $C_2H_5$, R" is $CH_3$, n is 1, Y is $C(C_2H_5)=CHCH_2CH_2$].

A small portion of a solution of 15 g. of 3-ethyl-6-(3,4-methylenedioxyphenyl)-3-hexenyl iodide (Preparation D1) in 20 ml. of anhydrous ether was added to 1 g. of magnesium turnings in 15 ml. of anhydrous ether. A crystal of iodine was added and the magnesium crushed with a stirring rod until reaction with the iodide was initiated. The rest of the iodide solution was then added at such a rate to cause gentle reflux. After the addition was complete, the mixture was stirred at room temperature for 1 hour. A solution of 3 g. of 2-butanone in 30 ml. of anhydrous ether was then added at such a rate that the ether refluxed gently. The reaction mixture was stirred for 30 minutes, then 5 ml. of water was cautiously added followed by 2.3 ml. of concentrated sulfuric acid in 20 ml. of water. The product was extracted with ether, the ether solution dried over anhydrous magnesium sulfate and concentrated. The residue was chromatographed on silica gel and eluted with the pentane-benzene-chloroform-ether solvent series. The desired product was brought out with chloroform-ether 9:1 to give 1.9 g. of 6-ethyl-3-methyl-9-(3,4-methylenedioxyphenyl)-6-nonen-3-ol as an amber liquid.

Anal. Calcd. for $C_{19}H_{28}O_3$: C, 74.96; H, 9.27. Found: C, 74.85; H, 9.26. Infrared (IR) (oil film) $\lambda_u^{max}$ 3.45ms + shldrs. (CH); 6.33–6.40mss, 6.74ms, 6.69ms (unsat. + arom + CH). Nuclear Magnetic Resonance (NMR) [20% $CDCl_3$, internal tetramethylsilane (TMS)] δ ppm (Ratio) 6.73(3) (arom); 5.93(2) (O—$CH_2$—O); 5.22(1) =CH; 0.8–2.8 (13) ($CH_2 \times 6$, OH); 1.15, 0.93, 0.92(9)(Me singlet + Me triplet × 2).

6-Ethyl-3-methyl-9-(3,4-methylenedioxyphenyl)-6-nonen-3-ol was found to have a minimum inhibitory concentration in vitro of 12 micrograms per milliliter against equine rhino virus.

6-Ethyl-3-methyl-9-(3,4-methylenedioxyphenyl)-6-nonen-3-ol was found to be pesticidal against yellow fever mosquito larvae at 1.7 ppm in water; and also effective against yellow mealworm pupae (tenebrio), dock beetle larvae and rhodnius prolixus nymph at 5–10 micrograms per insect.

By replacing the 2-butanone in the foregoing preparation by a molar equivalent amount of acetone, 1-hexen-4-one, nonan-4-one, cyclohexanone or cyclopentanone there can be obtained, respectively:

5-ethyl-2-methyl-8-(3,4-methylenedioxyphenyl)-5-octen-2-ol [I; Ar is 3,4-methylenedioxyphenyl, R' and R" are $CH_3$, n is 1, Y is $C(C_2H_5)=CHCH_2CH_2$], 4,7-diethyl-10-(3,4-methylenedioxyphenyl)-1,7-decadien-4-ol [I; Ar is 3,4-methylenedioxyphenyl, R' is $CH_2=CHCH_2$, R" is $C_2H_5$, n is 1, Y is $C(C_2H_5)=CHCH_2CH_2$], 5-(n-butyl)-8-ethyl-11-(3,4-methylenedioxyphenyl)-8-undecen-5-ol [I; Ar is 3,4-methylenedioxyphenyl, R' and R" are n-butyl, n is 1, Y is $C(C_2H_5)=CHCH_2CH_2$], 1-[3-ethyl-6-(3,4-methylenedioxyphenyl)-3-hexenyl]cyclohexanol [I; Ar is 3,4-methylenedioxyphenyl, R' and R" are together $(CH_2)_5$, n is 1, Y is $C(C_2H_5)=CHCH_2CH_2$], or 1-[3-ethyl-6-(3,4-methylenedioxyphenyl)-3-hexenyl]cyclopentanol [I; Ar is 3,4-methylenedioxyphenyl, R' and R" are together $(CH_2)_4$, n is 1, Y is $C(C_2H_5)=CHCH_2CH_2$].

By replacing the 3-ethyl-6-(3,4-methylenedioxyphenyl)-3-hexenyl iodide in the foregoing preparation by a molar equivalent amount of 6-(3,4-methylenedioxyphenyl)-3-hexenyl iodide (Preparation D2); 3-methyl-6-(3,4-methylenedioxyphenyl)-3-hexenyl iodide (Preparation D3); 3-ethyl-6-(3,4-dimethoxyphenyl)-3-hexenyl iodide (Preparation D4); 6-(4-methoxyphenyl)-3-hexenyl iodide (Preparation D5); 6-(4-methoxyphenyl)hexyl iodide (Preparation D6); 6-phenylhexyl iodide (Preparation D7); 6-(4-chlorophenyl)hexyl iodide (Preparation D8); 6-(p-tolyl)hexyl iodide (Preparation D9); 3-ethyl-6-(3,4-methylenedioxyphenyl)-3,5-hexadienyl iodide (Preparation D10); 3-isopropyl-6-(3,4-methylenedioxyphenyl)hexyl iodide; 3-butyl-6-(3,4-methylenedioxyphenyl)hexyl iodide, 6-(3,4-dichlorophenyl)hexyl iodide; 6-(2,4-dichlorophenyl)hexyl iodide; 6-(4-bromophenyl)hexyl iodide; 6-(4-fluorophenyl)hexyl iodide; 6-(4-trifluoromethoxyphenyl)hexyl iodide; or 6-(4-trifluoromethylphenyl)hexyl iodide, there can be obtained, respectively:

3-methyl-9-(3,4-methylenedioxyphenyl)-6-nonen-3-ol [I; Ar is 3,4-methylenedioxyphenyl, R' is $C_2H_5$, R" is $CH_3$, n is 1, Y is $CH=CHCH_2CH_2$];

3,6-dimethyl-9-(3,4-methylenedioxyphenyl)-6-nonen-3-ol [I; Ar is 3,4-methylenedioxyphenyl, R' is $C_2H_5$, R" is $CH_3$, n is 1, Y is $C(CH_3)=CHCH_2CH_2$];

6-ethyl-3-methyl-9-(3,4-dimethoxyphenyl)-6-nonen-3-ol [I; Ar is 3,4-$(CH_3O)_2C_6H_3$, R' is $C_2H_5$, R" is $CH_3$, n is 1, Y is $C(C_2H_5)=CHCH_2CH_2$];

3-methyl-9-(4-methoxyphenyl)-6-nonen-3-ol [I; Ar is 4-$CH_3OC_6H_4$, R' is $C_2H_5$, R" is $CH_3$, n is 1, Y is $CH=CHCH_2CH_2$];

3-methyl-9-(4-methoxyphenyl)nonan-3-ol [I; Ar is 4-CH$_3$OC$_6$H$_4$, R' is C$_2$H$_5$, R" is CH$_3$, n is 1, Y is CH$_2$CH$_2$CH$_2$CH$_2$];

3-methyl-9-phenylnonan-3-ol [I; Ar is C$_6$H$_5$, R' is C$_2$H$_5$, R" is CH$_3$, n is 1, Y is CH$_2$CH$_2$CH$_2$CH$_2$];

3-methyl-9-(4-chlorophenyl)nonan-3-ol [I; Ar is 4-ClC$_6$H$_4$, R' is C$_2$H$_5$, R" is CH$_3$, n is 1, Y is CH$_2$CH$_2$CH$_2$CH$_2$];

3-methyl-9-(p-tolyl)nonan-3-ol [I; Ar is 4-CH$_3$C$_6$H$_4$, R' is C$_2$H$_5$, R" is CH$_3$, n is 1, Y is CH$_2$CH$_2$CH$_2$CH$_2$];

3-methyl-6-ethyl-9-(3,4-methylenedioxyphenyl)-6,8-nonadien-3-ol [I; Ar is 3,4-methylenedioxyphenyl, R' is C$_2$H$_5$, R" is CH$_3$, n is 1, Y is C(C$_2$H$_5$)=CHCH=CH];

3-methyl-6-isopropyl-9-(3,4-methylenedioxyphenyl)nonan-3-ol [I; Ar is 3,4-methylenedioxyphenyl, R' is C$_2$H$_5$, R" is CH$_3$, n is 1, Y is CH(isopropyl)CH$_2$CH$_2$CH$_2$];

3-methyl-6-butyl-9-(3,4-methylenedioxyphenyl)nonan-3-ol [I; Ar is 3,4-methylenedioxyphenyl, R' is C$_2$H$_5$, R" is CH$_3$, n is 1, Y is CH(n-butyl)CH$_2$CH$_2$CH$_2$];

3-methyl-9-(3,4-dichlorophenyl)nonan-3-ol [I; Ar is 3,4-Cl$_2$C$_6$H$_3$, R' is C$_2$H$_5$, R" is CH$_3$, n is 1, Y is CH$_2$CH$_2$CH$_2$CH$_2$];

3-methyl-9-(2,4-dichlorophenyl)nonan-3-ol [I; Ar is 2,4-Cl$_2$C$_6$H$_3$, R' is C$_2$H$_5$, R" is CH$_3$, n is 1, Y is CH$_2$CH$_2$CH$_2$CH$_2$];

3-methyl-9-(4-bromophenyl)nonan-3-ol [I; Ar is 4-BrC$_6$H$_4$, R' is C$_2$H$_5$, R" is CH$_3$, n is 1, Y is CH$_2$CH$_2$CH$_2$CH$_2$];

3-methyl-9-(4-fluorophenyl)nonan-3-ol [I; Ar is 4-FC$_6$H$_4$, R' is C$_2$H$_5$, R" is CH$_3$, n is 1, Y is CH$_2$CH$_2$CH$_2$CH$_2$];

3-methyl-9-(4-trifluoromethoxyphenyl)nonan-3-ol [I; Ar is 4-F$_3$COC$_6$H$_4$, R' is C$_2$H$_5$, R" is CH$_3$, n is 1, Y is CH$_2$CH$_2$CH$_2$CH$_2$]; or 3-methyl-9-(4-trifluoromethylphenyl)nonan-3-ol [I; Ar is 4-F$_3$CC$_6$H$_4$, R' is C$_2$H$_5$, R" is CH$_3$, n is 1, Y is CH$_2$CH$_2$CH$_2$CH$_2$].

The foregoing iodide reactants can if desired, be replaced by the corresponding bromides.

EXAMPLE 2

(a) Ethyl 2-acetyl-5-ethyl-8-(3,4-methylenedioxyphenyl)-5-octenoate [X; R" is CH$_3$, R° is C$_2$H$_5$, Ar is 3,4-methylenedioxyphenyl, Y is C(C$_2$H$_5$)=CHCH$_2$CH$_2$].

A mixture of 10 g. of the lithium salt of ethyl acetoacetate (prepared from ethyl acetoacetate and n-butyllithium) and 9.6 g. of 3-ethyl-6-(3,4-methylenedioxyphenyl)-3-hexenyl iodide (Preparation D1) in 100 ml. of tetramethylurea was heated at 60° C. for 5 days. The reaction mixture was filtered, the filtrate concentrated in vacuo to a volume of about 20 ml., then diluted with 200 ml. of water and extracted with ether. The ether solution was washed with water and saturated sodium chloride solution, and dried over anhydrous magnesium sulfate. The dried ether solution was concentrated to remove the solvent and the residue was chromatographed on silica gel. The chromatograph column was eluted with pentane-benzene-ether solvent series which first removed unreacted iodide and then brought out the desired product, 2.4 g. of ethyl 2-acetyl-5-ethyl-8-(3,4-methylenedioxyphenyl)-5-octenoate as a yellow oil.

Anal. Calcd. for C$_{20}$H$_{28}$O$_5$: C, 69.98; H, 7.83. Found: C, 69.97; H, 7.86. IR (oil film) $\lambda_\mu^{max}$ 3.45mss + shldrs. (CH), 5.78mss, 5.86s (C=O); 6.15–6.30m, 6.67mss, 6.73s, 6.95mss (arom and CH). NMR (20% CDCl$_3$, internal TMS) δ ppm (Ratio) 6.63(3) (arom); 5.86(2) (O—CH$_2$—O); 5.10(1) (=CH); 4.17(2) (OCH$_2$ quartet); 3.33(1) [(O=C)$_2$—CH]; 1.7–2.8(13) (aliph. CH incl. COCH$_3$); 1.25(3), 0.90(3) (Me triplet × 2).

(b) 6-Ethyl-9-(3,4-methylenedioxyphenyl)-6-nonen-2-one [XI; R" is CH$_3$, Ar is 3,4-methylenedioxyphenyl, Y is C(C$_2$H$_5$)=CHCH$_2$CH$_2$].

A mixture of 31.5 g. (0.0875 mole) of ethyl 2-acetyl-5-ethyl-8-(3,4-methylenedioxyphenyl)-5-octenoate and 7.28 g. (0.13 mole) of potassium hydroxide in 100 ml. of methanol and 20 ml. of water was heated at reflux for 4 hours. An additional 7.28 g. of potassium hydroxide in 9 ml. of water was added and the mixture heated at reflux for about 16 hours under nitrogen. The reaction mixture was added to 100 ml. of water, cooled to 0°, acidified with 5% sulfuric acid and extracted three times with 250 ml. of ether. The ether layers were washed with dilute sodium bicarbonate and water, dried over anhydrous magnesium carbonate and concentrated to give 27 g. of yellow oil. The latter was chromatographed on 160 g. of silica gel and the column eluted with the pentane-benzene-ether solvent series. Benzene-ether 9:1 brought out the desired product, 8 g. of 6-ethyl-9-(3,4-methylenedioxyphenyl)-6-nonen-2-one as a light yellow oil.

Anal. Calcd. for C$_{18}$H$_{24}$O$_3$: C, 75.23; H, 8.06. Found: C, 74.77; H, 8.34. IR (oil film) $\lambda_\mu^{max}$ 3.45s + shldrs. (CH); 5.86s (C=O); 6.24m, 6.67s, 6.74s, 6.95s (arom + CH). NMR (20% CDCl$_3$, internal TMS) δ ppm (Ratio) 6.78(3) (arom); 5.97(2) (O—CH$_2$—O); 5.22(1) (—CH—), 1.5–2.9(15) (CH$_2$ × 6, C=O—CH$_3$); 0.96(3) (Me triplet).

6-Ethyl-9-(3,4-methylenedioxyphenyl)-6-nonen-2-one was found to have a minimum inhibitory concentration in vitro of 6–12 micrograms per milliliter against equine rhino virus.

6-Ethyl-9-(3,4-methylenedioxyphenyl)-6-nonen-2-one was found to be pesticidal against dock beetle larvae at 5 micrograms per insect.

(c) 7-Ethyl-3-methyl-10-(3,4-methylenedioxyphenyl)-7-decen-3-ol [I; Ar is 3,4-methylenedioxyphenyl, R' is C$_2$H$_5$, R" is CH$_3$, n is 2, Y is C(C$_2$H$_5$)=CHCH$_2$CH$_2$].

To 14.3 g. (0.05 mole) of 6-ethyl-9-(3,4-methylenedioxyphenyl)-6-nonen-2-one in 200 ml. of anhydrous ether was added 30 ml. (0.1 mole) of ethylmagnesium bromide (10 ml. of 3N ethereal solution) at −15° C. over a period of 5 minutes. The reaction mixture was allowed to warm to room temperature, stirred there for 90 minutes and then heated at reflux for 1 hour. The reaction mixture was cooled, 21 ml. of saturated ammonium chloride solution was added, and the mixture extracted twice with 250 ml. portions of ether. The ether solution was dried over anhydrous magnesium sulfate and concentrated to give 14.5 g. of oil. The latter was chromatographed on 180 g. of silica gel and the column eluted with the pentane-benzene-chloroform solvent series. The material brought out by benzene and benzene-chloroform mixtures was rechromatographed on 120 g. of silica gel. Elution with benzene containing 10–50% chloroform provided 3.1 g. of 7-ethyl-3-methyl-10-(3,4-methylenedioxyphenyl)-7-decen-3-ol as a yellow oil.

Anal. Calcd. for C$_{20}$H$_{30}$O$_3$: C, 75.43; H, 9.49. Found: C, 75.91; H, 9.68. IR (oil film) $\lambda_\mu^{max}$ 2.92m + shldrs. (OH); 3.40s + shldrs. (CH); 6.24m, 6.65mss, 6.71s, 6.94mss + shldrs. (arom, CH). NMR (20% CDCl$_3$, internal TMS) δ ppm (Ratio) 6.77(3) arom; 5.93(2)

(O—CH$_2$—O); 5.20(1) (=CH—); 1.25-2.85(15) (CH$_2$ × 7 + OH); 1.12, 0.92, 0.88 (Me singlet, Me triplet × 2).

7-Ethyl-3-methyl-10-(3,4-methylenedioxyphenyl)-7-decen-3-ol was found to have a minimum inhibitory concentration in vitro against rhino-2, equine rhino, para-influenza and respiratory syncitial virus of 0.3, 6, 12 and 6 micrograms per milliliter, respectively.

7-Ethyl-3-methyl-10-(3,4-methylenedioxyphenyl)-7-decen-3-ol was found to be pesticidal against yellow mealworm pupae (tenebrio) and rhodnius prolixus nymph at 10 micrograms per insect.

EXAMPLE 3

8-Ethyl-4-methyl-11-(3,4-methylenedioxyphenyl)-1,8-undecadien-4-ol [I; Ar is 3,4-methylenedioxyphenyl, R' is CH=CHCH$_2$, R" is CH$_3$, $n$ is 2, Y is C(C$_2$H$_5$)=CHCH$_2$CH$_2$] was prepared from 6 g. of 6-ethyl-9-(3,4-methylenedioxyphenyl)-6-nonen-2-one (Example 2, part b) and allylmagnesium bromide (0.1 mole in 250 ml. of ether) according to the procedure described above in Example 2. The product was chromatographed on 100 g. of silica gel, and the column was eluted with pentane containing increasing amounts of benzene and finally with benzene alone. The later fractions brought out the desired product, 8-ethyl-4-methyl-11-(3,4-methylenedioxyphenyl)-1,8-undecadien-4-ol as a yellow oil.

Anal. Calcd. for C$_{21}$H$_{30}$O$_3$: C, 76.32; H, 9.15. Found: C, 75.50; H, 9.09. IR (oil film) $\lambda_\mu^{max}$ 2.94mms + shldrs. (OH); 3.45s + shldrs. (CH); 6.11m, 6.24m, 6.66s, 6.72s, 6.94s (unsat. arom, CH). NMR (20% CDCl$_3$, internal TMS) δ ppm (Ratio) 6.75(3) (arom); 5.93(2) (O—CH$_2$—O); 4.9-6.3(4) (CH$_2$=CH—, =CH); 1.3-2.8(15) (CH$_2$ × 7 + OH); 1.15, 0.92(6) (Me singlet, Me triplet).

8-Ethyl-4-methyl-11-(3,4-methylenedioxyphenyl)-1,8-undecadien-4-ol was found to have a minimum inhibitory concentration in vitro against equine rhino virus of 12 micrograms per milliliter.

8-Ethyl-4-methyl-11-(3,4-methylenedioxyphenyl)-1,8-undecadien-4-ol was found to be pesticidal against yellow mealworm pupae (tenebrio) and rhodnius prolixus nymph at 10 micrograms per insect.

EXAMPLE 4

6-Ethyl-2-methyl-9-(3,4-methylenedioxyphenyl)-6-nonen-2-ol [I; Ar is 3,4-methylenedioxyphenyl, R' and R" are CH$_3$, $n$ is 2, Y is C(C$_2$H$_5$)=CHCH$_2$CH$_2$] was prepared from 14.3 g. of 6-ethyl-9-(3,4-methylenedioxyphenyl)-6-nonen-2-one (Example 2, part b) and methylmagnesium bromide (66 ml. of 3 molar in tetrahydrofuran) according to the procedure described above in Example 2. The product (14 g. of oil) was chromatographed twice on activated magnesium silicate and the column was eluted with pentane containing increasing amounts of benzene. The later fractions brought out the desired product, 6-ethyl-2-methyl-9-(3,4-methylenedioxyphenyl)-6-nonen-2-ol as a light yellow oil.

Anal. Calcd. for C$_{19}$H$_{28}$O$_3$: C, 74.95; H, 9.27. Found: C, 75.07; H, 9.29. IR (oil film) $\lambda_\mu^{max}$ 2.95m (OH); 3.40mss + shldrs. (CH), 6.22m, 6.65mss, 6.71s, 6.92mss (arom, CH). NMR (20% CDCl$_3$, internal TMS) δ ppm (Ratio) 6.68(3) (arom); 5.90(2) (O—CH$_2$—O); 5.13(1) (=CH); 1.3-2.8(13) (CH$_2$ × 6 + OH); 1.2(6) (CMe$_2$); 0.92(3) (Me triplet).

6-Ethyl-2-methyl-9-(3,4-methylenedioxyphenyl)-6-nonen-2-ol was found to have a minimum inhibitory concentration in vitro against equine rhino virus of 12 micrograms per milliliter.

6-Ethyl-2-methyl-9-(3,4-methylenedioxyphenyl)-6-nonen-2-ol was found to be pesticidal against yellow mealworm pupae (tenebrio) at 1 microgram per insect and against rhodnius prolixus nymph at 3 micrograms per insect.

EXAMPLE 5

(a) Ethyl 2-acetyl-8-(3,4-methylenedioxyphenyl)-5-octenoate [X; R" is CH$_3$, R° is C$_2$H$_5$, Ar is 3,4-methylenedioxyphenyl, Y is CH=CHCH$_2$CH$_2$].

A mixture of 28.3 g. (0.1 mole) of 6-(3,4-methylenedioxyphenyl)-3-hexenyl bromide and 21 g. (0.15 mole) of lithium ethylacetoacetate in 200 ml. of dimethylformamide was heated under nitrogen with stirring at 55°–60° C. for 2 days. The reaction mixture was concentrated in vacuo and the residue partitioned between water and methylene dichloride. The methylene dichloride layer was washed with 5% aqueous sulfuric acid, water, 5% aqueous sodium bicarbonate and water, and dried over anhydrous magnesium sulfate. The ether solution was concentrated to afford ethyl 2-acetyl-8-(3,4-methylenedioxyphenyl)-5-octenoate as a yellow oil, used directly in the following reaction.

(b) 9-(3,4-Methylenedioxyphenyl)-6-nonen-2-one [XI; R" is CH$_3$, Ar is 3,4-methylenedioxyphenyl, Y is CH=CHCH$_2$CH$_2$] was prepared from 27 g. of ethyl 2-acetyl-8-(3,4-methylenedioxyphenyl)-5-octenoate and potassium hydroxide in aqueous methanol according to the procedure described above in Example 2, part (b). The neutral fraction of the product was chromatographed on 390 g. of activated magnesium silicate and the column was eluted with pentane containing increasing amounts of benzene. The later fractions brought out the desired product, 12.3 g. of 9-(3,4-methylenedioxyphenyl)-6-nonen-2-one.

(c) 3-Methyl-10-(3,4-methylenedioxyphenyl)-7-decen-3-ol [I; Ar is 3,4-methylenedioxyphenyl, R' is C$_2$H$_5$, R" is CH$_3$, $n$ is 2, Y is CH=CHCH$_2$CH$_2$] was prepared from 12.3 g. of 9-(3,4-methylenedioxyphenyl)-6-nonen-2-one and 66 ml. of ethylmagnesium bromide (3 molar in ether) according to the procedure described above in Example 2. The product was chromatographed on 330 g. of activated magnesium silicate and the column was eluted with pentane containing increasing amounts of benzene. The later fractions brought out the desired product, 7.8 g. of 3-methyl-10-(3,4-methylenedioxyphenyl)-7-decen-3-ol as a pale yellow oil.

Anal. Calcd. for C$_{18}$H$_{26}$O$_3$: C, 74.44; H, 9.02. Found: C, 74.83; H, 9.03. IR (oil film) $\lambda_\mu^{max}$ 2.95mss + shldrs. (OH); 3.45s + shldrs. (CH); 6.15m, 6.24mms, 6.66s, 6.73s, 6.95s + shldrs. (unsat. arom, CH).

EXAMPLE 6

(a) Ethyl 2-propionyl-5-ethyl-8-(3,4-methylenedioxyphenyl)-5-octenoate [X; Ar is 3,4-methylenedioxyphenyl, R" and R° are C$_2$H$_5$, Y is C(C$_2$H$_5$)=CHCH$_2$CH$_2$] was prepared from 10 g. of 3-ethyl-6-(3,4-methylenedioxyphenyl)-3-hexenyl iodide (Preparation D1) and 4.6 g. of the lithium salt of ethyl 3-oxovalerate in 100 ml. of dimethylformamide by the procedure described above in Example 2, part (a). The product was chromatographed on silica gel and diluted with chloroform containing 20% benzene to give 5.5 g. of ethyl 2-propionyl-5-ethyl-8-(3,4- methylenedioxyphenyl)5-octenoate as an amber liquid.

(b) 7-Ethyl-10-(3,4-methylenedioxyphenyl)-7-decen-3-one [XI; R" is $C_2H_5$, Ar is 3,4-methylenedioxyphenyl, Y is $C(C_2H_5)=CHCH_2CH_2$] can be prepared from ethyl 2-propionyl-5-ethyl-8-(3,4-methylenedioxyphenyl)-5-octenoate and potassium hydroxide in aqueous methanol according to the procedure described in Example 2, part (b).

(c) 7-Ethyl-3-isopropyl-10-(3,4-methylenedioxyphenyl)-7-decen-3-ol [I; Ar is 3,4-methylenedioxyphenyl, R' is $CH(CH_3)_2$, R" is $C_2H_5$, $n$ is 2, Y is $C(C_2H_5)=CHCH_2CH_2$] can be prepared from 7-ethyl-10(3,4-methylenedioxyphenyl)-7-decen-3-one and isopropylmagnesium bromide according to the procedure described in Example 2, part (c).

EXAMPLE 7

(a) Ethyl 2-butyryl-5-ethyl-8-(3,4-methylenedioxyphenyl)-5-octenoate [X; Ar is 3,4-methylenedioxphenyl, R" is $CH_2CH_2CH_3$, R° is $C_2H_5$, Y is $C(C_2H_5)=CHCH_2CH_2$] was prepared from 20 g. of 3-ethyl-6-(3,4-methylenedioxyphenyl)-3-hexenyl iodide (Preparation D1) and 12 g. of the lithium salt of ethyl 3-oxohexanoate according to the procedure described above in Example 2. There was thus obtained 11.57 g. of ethyl 2-butyryl-5-ethyl-8-(3,4-methylenedioxyphenyl)-5-octenoate as a light yellow oil.

Anal. Calcd. for $C_{23}H_{32}O_5$: C, 71.11; H, 8.30. Found: C, 70.89; H, 8.54. IR (oil film) $\lambda_\mu^{max}$ 3.45mss + shldrs. (CH); 5.78mss, 5.91s (C=O); 6.24m, 6.75mss, 6.68 shldr. 6.96mss (arom and CH). NMR (20% $CDCl_3$, internal TMS) $\delta$ ppm (Ratio) 6.73(3) (arom); 5.93(2) (O—$CH_2$—O); 5.17(1) (=CH); 4.22(2) ($OCH_2CH_3$ quartet); 3.42(1+) [(O=C)$_2$CH], 0.7–2.8(23) (aliph. CH incl. Me triplet × 3).

(b) 8-Ethyl-11-(3,4-methylenedioxyphenyl)-8-undecen-4-one [XI; R" is $CH_2CH_2CH_3$, Ar is 3,4-methylenedioxyphenyl, Y is $C(C_2H_5)=CHCH_2CH_2$] can be prepared from ethyl 2-butyryl-5-ethyl-8-(3,4-methylenedioxyphenyl)-5-octenoate and potassium hydroxide in aqueous methanol according to the procedure described in Example 2, part (b).

(c) 3-Allyl-8-ethyl-11-(3,4-methylenedioxyphenyl)-8-undecen-4-ol [I; Ar is 3,4-methylenedioxyphenyl, R' is $CH_2CH=CH_2$, R" is $CH_2CH_2CH_3$, $n$ is 2, Y is $C(C_2H_5)=CHCH_2CH_2$] can be prepared from 8-ethyl-11-(3,4-methylenedioxyphenyl)-8-undecen-4-one and allylmagnesium bromide according to the procedure described in Example 2, part (c).

By replacing the 3-ethyl-6-(3,4-methylenedioxyphenyl)3-hexenyl iodide in Example 2, part (a), by a molar equivalent amount of 6-(3,4-methylenedioxyphenyl)-3-hexenyl iodide (Preparation D2); 3-methyl-6-(3,4-methylenedioxyphenyl)-3-hexenyl iodide (Preparation D3); 3-ethyl-6-(3,4-dimethoxyphenyl)-3-hexenyl iodide (Preparation D4); 6-(4-methoxyphenyl)-3-hexenyl iodide (Preparation D5); 6-(4-methoxyphenyl)hexyl iodide (Preparation D6); 6-phenylhexyl iodide (Preparation D7); 6-(4-chlorophenyl)hexyl iodide (Preparation D8); 6-(p-tolyl)hexyl iodide (Preparation D9); 3-ethyl-6-(3,4-methylenedioxyphenyl)-3,5-hexadienyl iodide (Preparation D10); 3-isopropyl-6-(3,4-methylenedioxyphenyl)hexyl iodide; 3-butyl-6-(3,4-methylenedioxyphenyl)hexyl iodide; 6-(3,4-dichlorophenyl)hexyl iodide; 6-(2,4-dichlorophenyl)hexyl iodide; 6-(4-bromophenyl)hexyl iodide; 6-(4-fluorophenyl)hexyl iodide; 6-(4-trifluoromethoxyphenyl)hexyl iodide; or 6-(4-trifluoromethylphenyl)hexyl iodide and then carrying out the hydrolytic procedure of step (b) of Example 2, there can be obtained, respectively:

9-(3,4-methylenedioxyphenyl)-6-nonen-2-one [XI; R" is $CH_3$, Ar is 3,4-methylenedioxyphenyl, Y is $CH=CHCH_2CH_2$];

6-methyl-9-(3,4-methylenedioxyphenyl)-6-nonen-2-one [XI; R" is $CH_3$, Ar is 3,4-methylenedioxyphenyl, Y is $C(CH_3)=CHCH_2CH_2$];

6-ethyl-9-(3,4-dimethoxyphenyl)-6-nonen-2-one [XI; R" is $CH_3$, Ar is 3,4-$(CH_3O)_2C_6H_3$, Y is $C(C_2H_5)=CHCH_2CH_2$];

9-(4-methoxyphenyl)-6-nonen-2-one [XI; R" is $CH_3$, Ar is 4-$CH_3OC_6H_4$, Y is $CH=CHCH_2CH_2$];

9-(4-methoxyphenyl)nonan-2-one [XI; R" is $CH_3$, Ar is 4-$CH_3OC_6H_4$, Y is $CH_2CH_2CH_2CH_2$];

9-phenylnonan-2-one [XI; R" is $CH_3$, Ar is $C_6H_5$, Y is $CH_2CH_2CH_2CH_2$];

9-(4-chlorophenyl)nonan-2-one [XI; R" is $CH_3$, Ar is 4-$ClC_6H_4$, Y is $CH_2CH_2CH_2CH_2$];

9-(p-tolyl)nonan-2-one [XI; R" is $CH_3$, Ar is 4-$CH_3C_6H_4$, Y is $CH_2CH_2CH_2CH_2$];

6-ethyl-9-(3,4-methylenedioxyphenyl)-6,8-nonadien-2-one [XI; R" is $CH_3$, Ar is 3,4-methylenedioxphenyl, Y is $C(C_2H_5)=CHCH=CH$];

6-isopropyl-9-(3,4-methylenedioxyphenyl)-6-nonen-2-one [XI; R" is $CH_3$, Ar is 3,4-methylenedioxyphenyl, Y is $C(iso-Pr)=CHCH_2CH_2$];

6-butyl-9-(3,4-methylenedioxyphenyl)-6-nonen-2-one [XI; R" is $CH_3$, Ar is 3,4-methylenedioxyphenyl, Y is $C(n-Bu)=CHCH_2CH_2$];

9-(3,4-dichlorophenyl)nonan-2-one [XI; R" is $CH_3$, Ar is 3,4-$Cl_2C_6H_3$, Y is $CH_2CH_2CH_2CH_2$];

9-(2,4-dichlorophenyl)nonan-2-one [XI; R" is $CH_3$, Ar is 2,4-$Cl_2C_6H_3$, Y is $CH_2CH_2CH_2CH_2$];

9-(4-bromophenyl)nonan-2-one [XI; R" is $CH_3$, Ar is 4-$BrC_6H_4$, Y is $CH_2CH_2CH_2CH_2$];

9-(4-fluorophenyl)nonan-2-one [XI; R" is $CH_3$, Ar is 4-$FC_6H_4$, Y is $CH_2CH_2CH_2CH_2$];

9-(4-trifluoromethoxyphenyl)nonan-2-one [XI; R" is $CH_3$, Ar is 4-$F_3COC_6H_4$, Y is $CH_2CH_2CH_2CH_2$]; or 9-(4-trifluoromethylphenyl)nonan-2-one [XI; R" is $CH_3$, Ar is 4-$F_3CC_6H_4$, Y is $CH_2CH_2CH_2CH_2$].

The foregoing ketones of formula XI can be caused to react with ethylmagnesium bromide according to the procedure of Example 2, part (c) to produce the following carbinols, respectively:

3-methyl-10-(3,4-methylenedioxyphenyl)-7-decen-3-ol [I; Ar is 3,4-methylenedioxyphenyl, R' is $C_2H_5$, R" is $CH_3$, $n$ is 2, Y is $CH=CHCH_2CH_2$];

3,7-dimethyl-10-(3,4-methylenedioxyphenyl)-7-decen-3-ol [I; Ar is 3,4-methylenedioxyphenyl, R' is $C_2H_5$, R" is $CH_3$, $n$ is 2, Y is $C(CH_3)=CHCH_2$];

7-ethyl-3-methyl-10-(3,4-dimethoxyphenyl)-7-decen-3-ol [I; Ar is 3,4-$(CH_3O)_2C_6H_3$, R' is $C_2H_5$, R" is $CH_3$, $n$ is 2, Y is $C(C_2H_5)=CHCH_2CH_2$];

3-methyl-10-(4-methoxyphenyl)-7-decen-3-ol [I; Ar is 4-$CH_3OC_6H_4$, R' is $C_2H_5$, R" is $CH_3$, $n$ is 2, Y is $CH=CHCH_2CH_2$];

3-methyl-10-(4-methoxyphenyl)decan-3-ol [I; Ar is 4-$CH_3OC_6H_4$, R' is $C_2H_5$, R" is $CH_3$, $n$ is 2, Y is $CH_2CH_2CH_2CH_2$];

3-methyl-10-phenyldecan-3-ol [I; Ar is $C_6H_5$, R' is $C_2H_5$, R" is $CH_3$, $n$ is 2, Y is $CH_2CH_2CH_2CH_2$];

3-methyl-10-(4-chlorophenyl)decan-3-ol [I; Ar is 4-ClC$_6$H$_4$, R' is C$_2$H$_5$, R'' is CH$_3$, n is 2, Y is CH$_2$CH$_2$CH$_2$CH$_2$];

3-methyl-10-(p-tolyl)decan-3-ol [I; Ar is 4-CH$_3$C$_6$H$_4$, R' is C$_2$H$_5$, R'' is CH$_3$, n is 2, Y is CH$_2$CH$_2$CH$_2$CH$_2$];

7-ethyl-3-methyl-10-(3,4-methylenedioxyphenyl)-7,9-decadien-3-ol [I; Ar is 3,4-methylenedioxyphenyl, R' is C$_2$H$_5$, R'' is CH$_3$, n is 2, Y is C(C$_2$H$_5$)=CHCH=CH];

7-isopropyl-3-methyl-10-(3,4-methylenedioxyphenyl)-7-decen-3-ol [I; Ar is 3,4-methylenedioxyphenyl, R' is C$_2$H$_5$, R'' is CH$_3$, n is 2, Y is C(iso-Pr)=CHCH$_2$CH$_2$];

7-butyl-3-methyl-10-(3,4-methylenedioxyphenyl)-7-decen-3-ol [I; Ar is 3,4-methylenedioxyphenyl, R' is C$_2$H$_5$, R'' is CH$_3$, n is 2, Y is C(n-Bu)=CHCH$_2$CH$_2$];

3-methyl-10-(3,4-dichlorophenyl)decan-3-ol [I; Ar is 3,4-Cl$_2$C$_6$H$_3$, R' is C$_2$H$_5$, R'' is CH$_3$, n Y is CH$_2$CH$_2$CH$_2$CH$_2$];

3-methyl-10-(2,4-dichlorophenyl)decan-3-ol [I; Ar is 2,4-Cl$_2$C$_6$H$_3$, R' is C$_2$H$_5$, R'' is CH$_3$, n is 2, Y is CH$_2$CH$_2$CH$_2$CH$_2$];

3-methyl-10-(4-bromophenyl)decan-3-ol [I; Ar is 4-BrC$_6$H$_4$, R' is C$_2$H$_5$, R'' is CH$_3$, n is 2, Y is CH$_2$CH$_2$CH$_2$CH$_2$];

3-methyl-10-(4-fluorophenyl)decan-3-ol [I; Ar is 4-FC$_6$H$_4$, R' is C$_2$H$_5$, R'' is CH$_3$, n is 2, Y is CH$_2$CH$_2$CH$_2$CH$_2$];

3-methyl-10-(4-trifluoromethoxyphenyl)decan-3-ol [I; Ar is 4-F$_3$COC$_6$H$_4$, R' is C$_2$H$_5$, R'' is CH$_3$, n is 2, Y is CH$_2$CH$_2$CH$_2$CH$_2$]; or 3-methyl-10-(4-trifluoromethylphenyl)decan-3-ol [I; Ar is 4-F$_3$CC$_6$H$_4$, R' is C$_2$H$_5$, R'' is CH$_3$, n is 2, Y is CH$_2$CH$_2$CH$_2$CH$_2$].

By procedures analogous to those described above in Example 2, 3-ethyl-6-(3,4-methylenedioxphenyl)-3-hexenyl iodide can be treated with the lithium salt of 2-carbomethoxycyclohexane to afford 2-carbomethoxy-2-[3-ethyl-6-(3,4-methylenedioxyphenyl)3-hexenyl]cyclohexanone, which can be hydrolyzed and decarboxylated to give 2-[3-ethyl-6-(3,4-methylenedioxyphenyl)-3-hexenyl]cyclohexanone [XIV; Ar is 3,4-methylenedioxyphenyl, Y is C(C$_2$H$_5$)=CHCH$_2$CH$_2$, m is 2]. The latter can be further reacted with methylmagnesium bromide to produce 1-methyl-2-[3-ethyl-6(3,4-methylenedioxyphenyl)-3-hexenyl]cyclohexanol [XV; Ar is 3,4-methylenedioxyphenyl, R' is CH$_3$, Y is C(C$_2$H$_5$)=CHCH$_2$CH$_2$, m is 2].

EXAMPLE 8

2-[3-Ethyl-6-(3,4-methylenedioxyphenyl)-3-hexenyl]cyclohexanone [XIV; Ar is 3,4-methylenedioxyphenyl, Y is C(C$_2$H$_5$)=CHCH$_2$CH$_2$, m is 2].

A mixture of 20 g. (0.056 mole) of 3-ethyl-6-(3,4-methylenedioxyphenyl)-3-hexenyl iodide and 21 g. (0.14 mole) of 1-(N-pyrrolidyl)cyclohex-1-ene in 250 ml. of absolute ethanol was heated at reflux for 20 hours under nitrogen. The reaction mixture was concentrated in vacuo to a 150 ml. volume and added to 100 ml. of water. This mixture was heated to 80° C. for 70 minutes, then at reflux for 10 minutes and cooled. It was then extracted three times with ether and the combined ether solutions washed successively with 5% hydrochloric acid, water, 5% sodium bicarbonate and water, dried over anhydrous magnesium sulfate and concentrated in vacuo. The residue was chromatographed on a column of 160 g. of silica gel, and the column was eluted with the pentane-benzene-chloroform-ether solvet series.

The fractions between pentane-benzene 8:2 and 100% chloroform brought out the desired product as a yellow oil.

Anal. Calcd. for C$_{21}$H$_{28}$O$_3$: C, 76.79; H, 8.59 Found: C, 77.08; H, 8.97. IR (oil film) $\lambda_\mu^{max}$ 3.44s + shldrs. (CH); 5.86s (C=O); 6.15w, 6.24wm, 6.29w, 6.66mss, 6.73s, 6.94s, 6.94mss (unsat. arom, CH). NMR (20% CDCl$_3$, internal TMS) $\delta$ ppm (Ratio) 7.3($\frac{1}{2}$) (CHCl$_3$); 6.7(3) (arom); 5.88(2) (O-CH$_2$-O); 5.13(1) (=CH); 0.7-3.0 (22) (remaining aliphatic CH).

2-[3-Ethyl-6-(3,4-methylenedioxyphenyl)-3-hexenyl]cyclohexanone was found to be pesticidal against mealworm pupae (tenebrio) and rhodnius prolixus nymph at 10 micrograms per insect.

2-[3-Ethyl-6-(3,4-methylenedioxyphenyl)-3-hexenyl]cyclohexanone can be treated with allylmagnesium bromide according to the procedure of Example 2, part (c) to give 1-allyl-2-[3-ethyl-6-(3,4-methylenedioxyphenyl)-3-hexenyl]cyclohexanol [XV; Ar is 3,4-methylenedioxyphenyl, Y is C(C$_2$H$_5$)=CHCH$_2$CH$_2$, R' is CH$_2$CH=CH$_2$, m is 2].

EXAMPLE 9

2-[3-Ethyl-6-(3,4-methylenedioxyphenyl)-3-hexenyl]cyclopentanone

[XIV; Ar is 3,4-methylenedioxyphenyl, Y is C(C$_2$H$_5$(=CHCH$_2$CH$_2$, m is 1] was prepared from 26 g. of 3-ethyl-6-(3,4-methylenedioxyphenyl)-3-hexenyl iodide and 20 g. of 1-(N-pyrrolidyl)cyclopent-1-ene according to the procedure described above in Example 8. There was thus obtained 8.6 g. of 2-[3-ethyl-6-(3,4-methylenedioxyphenyl)-3-hexenyl]cyclopentanone as a light amber oil.

Anal. Calcd. for C$_{20}$H$_{26}$O$_3$: C 76.40; H, 8.34. Found: C, 76.52; H, 8.33. IR (oil film) $\lambda_\mu^{max}$ 3.45s + shldrs. (CH); 5.76s (cyclopentanone C=O); 6.11m (C=C); 6.24m, 6.66mss, 6.72s, 6.95mss (arom + CH). NMR (20% CDCl$_3$, internal TMS) $\delta$ ppm (Ratio) 6.72(3) (arom); 5.93(2) (O-CH$_2$-O), 5.17(1) (=CH); 0.7-2.8 (20) (aliph. CH incl. Me triplet).

2-[3-Ethyl-6-(3,4-methylenedioxyphenyl)-3-hexenyl]cyclopentanone was found to have a minimum inhibitory concentration in vitro against equine rhino virus of about 6 micrograms per milliliter.

2-[3-Ethyl-6-(3,4-methylenedioxyphenyl)-3-hexenyl]cyclopentanone was found to be pesticidal against yellow mealworm pupae (tenebrio) at 10 micrograms per insect, dock beetle larvae at 5 micrograms per insect, yellow fever mosquito larvae at 6.6 ppm in water, and against rhodnius proxlixus nymph at 3 micrograms per insect.

2-[3-Ethyl-6-(3,4-methylenedioxyphenyl)-3-hexenyl]cyclopentanone can be treated with ethylmagnesium bromide according to the procedure of Example 2, part (c) to give 1-ethyl-2-[3-ethyl-6-(3,4-methylenedioxyphenyl)-3-hexenyl]cyclopentanol [XV; Ar is 3,4-methylenedioxyphenyl, Y is C(C$_2$H$_5$)=CHCH$_2$CH$_2$, R' is C$_2$H$_5$, m is 1].

We claim:

1. A compound of the formula

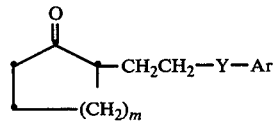

wherein Y is selected from the group consisting of

and 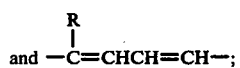

R is hydrogen or lower-alkyl of 1 to 4 carbon atoms; m is 1 or 2; and

Ar is phenyl or phenyl substituted by 3,4-methylenedioxy or one or two monovalent substituents selected from the group consisting of lower-alkyl of 1 to 4 carbon atoms, lower-alkoxy of 1 to 4 carbon atoms, halogen, trifluoromethyl and trifluoromethoxy.

2. A compound according to claim 1 wherein Ar is 3,4-methylenedioxyphenyl and Y is $C(R)=CHCH_2CH_2$.

3. 2-[3-Ethyl-6-(3,4-methylenedioxyphenyl)-3-hexenyl]cyclohexanone, according to claim 2.

4. 2-[3-Ethyl-6-(3,4-methylenedioxyphenyl)-3-hexenyl]cyclopentanone, according to claim 2.

* * * * *

UNITED STATES PATENT AND TRADEMARK OFFICE
CERTIFICATE OF CORRECTION

PATENT NO. : 4,125,714

DATED : November 14, 1978

INVENTOR(S) : Guy D. Diana and William B. Hinshaw, Jr.

It is certified that error appears in the above-identified patent and that said Letters Patent are hereby corrected as shown below:

Cover page, under [56], "Shippon" should read --Shippen--.

Column 2, line 65, "catalyst or" should read --catalyst to--.

Signed and Sealed this

Tenth Day of April 1979

[SEAL]

Attest:

RUTH C. MASON
Attesting Officer

DONALD W. BANNER
Commissioner of Patents and Trademarks